United States Patent [19]
Guyot et al.

[11] Patent Number: 4,748,977
[45] Date of Patent: Jun. 7, 1988

[54] MINERAL FIBER-BASED ABSORBENT MATERIAL

[75] Inventors: Daniel Guyot, Rantigny; Jean-Baptiste Rieunier, Nogent Sur Oise; Michel Conche, Villiers St-Paul, all of France

[73] Assignee: Isover Saint-Gobain, Courbevoie, France

[21] Appl. No.: 809,730

[22] Filed: Dec. 17, 1985

[30] Foreign Application Priority Data

Dec. 17, 1984 [FR] France ................................. 84 19244

[51] Int. Cl.$^4$ ............................................. A61L 15/00
[52] U.S. Cl. ..................................... 128/156; 428/222; 428/280; 428/288; 428/297; 428/903; 428/913; 428/299; 604/358; 604/365
[58] Field of Search ............... 428/280, 288, 913, 300, 428/299, 326, 222, 903, 297; 65/6, 8; 128/156; 604/357, 358, 365

[56] References Cited

U.S. PATENT DOCUMENTS

| 3,344,789 | 10/1967 | Arnold et al. | 128/287 |
| 4,286,977 | 9/1981 | Klein | 428/288 |
| 4,451,276 | 5/1984 | Barthe et al. | 65/6 |
| 4,463,048 | 7/1984 | Dickson et al. | 428/280 |

FOREIGN PATENT DOCUMENTS 0091381 12/1983 European Pat. Off. .

Primary Examiner—James J. Bell
Attorney, Agent, or Firm—Oblon, Fisher, Spivak, McClelland & Maier

[57] ABSTRACT

A fibrous mineral material serving as an absorbent, especially for hygienic products such as diapers, sanitary napkins, bandages and similar products, is comprised at least partially of these mineral fibers, which have a specific surface area greater than 0.25 m$^2$/g. The material has an appreciably greater absorption capacity than the regularly-used cellulose fluff-based products.

28 Claims, No Drawings

MINERAL FIBER-BASED ABSORBENT MATERIAL

BACKGROUND OF THE INVENTION

1. Field of the Invention

The invention pertains to a mineral fibrous material which serves as an absorbent, especially for hygienic products such as diapers, sanitary napkins, bandages and similar products.

2. Background of the Prior Art

Materials intended for this type of use must satisfy multiple criteria. They must especially possess a satisfactory absorbent capacity.

These materials must also be perfectly innocuous in the intended usage, and, in a more general manner, they must meet all of the requirements for hygienic products, especially those which are utilized in direct contact with the body.

The choice of these materials results from their unique set of considerations, which mainly involves their specific properties for this type of use, but also concerns their relatively low cost.

The latter consideration led recently to the development of the utilization of cellulose fibers produced from wood through the use of paper production techniques. These fibers are prepared in the form of what is termed "fluff", i.e., an interlocking product having a low mass by volume. These are short, irregular fibers which, for this reason, form a material having a low degree of cohesion and, overall, whose mechanical properties are modest, if not poorly suited, for the principally intended use. Especially lacking cohesion, the fluff is normally utilized in combination with other materials. Thus, the fluff serving as an absorbent for diapers is always placed inside a covering which serves as its support.

Moreover, the absorbent capacity of these fluffs is limited, as shown in comparative examples provided below.

Other considerations indicate that the fluff is not entirely satisfactory. Thus, because of the very short fibers of which it is comprised, it possesses a poor resistance to compression, whether in its production or in its use. Once it is compressed, its natural tendency to recover its initial volume is very small, and, as a result, its absorbent capacity is reduced considerably.

In the same manner, sinking under weight in the damp state, which constitutes an important characteristic for the use of these materials, is very great, about 50%.

Measures have been proposed to eliminate this mechanical drawback. This pertains especially to the reinforcement of the fluff by mixing it with other materials. In addition to the fact that it is not always convenient to obtain a perfectly homogeneous satisfactory combination, the formation of these compound materials robs the fluff of the advantage constituted by its low cost.

Moreover, the fluff, in the raw state, has a yellow or brown color, which is undesirable for hygienic products. Bleaching them through the use of traditional techniques, especially in the paper production industry, is possible, but entails additional costs, which are still higher as it is necessary to proceed with a subsequent accelerated neutralization of the residues of the chemical agents which are used.

Synthetic organic products have also been proposed to constitute this type of absorbent material. This pertains especially to grafted cellulose fiber-based products. Their absorbent capacity is normally very high, but, due to their high production cost, their uses are restricted.

This also pertains to compound products comprising a fibrous support in which particles or powders of products, which are of various natures, but which present a particularly high degree of absorbency, are dispersed. In addition to their high cost, these absorbent products contribute no mechanical qualities to the overall product. Moreover, their absorbent properties can be limited in use by their tendency to form clusters.

Mineral fiber felts have already been proposed as absorbent materials, especially as a means to fight marine pollution due to hydrocarbons. Other industrial applications also call directly or indirectly on the absorbent properties of the mineral fiber felts, especially glass fiber felts.

In these applications, the felts chosen due to their cost are the type which normally serve in areas in which production is more abundant, namely, that of the felts intended for insulation. Because of the characteristics required for these uses, combined with the production cost imperatives, these products cannot be utilized for physical hygiene.

Specifically, in the most widespread commercial products, the dimensional characteristics of the fibers and notably the presence of fibers having a diameter of about 10 micrometers or more, even in small proportions, causes irritations in contact with the skin which makes them inappropriate for this purpose.

Long, fine and highly regular mineral fibers are also known and produced for highly specialized applications. These fibers are normally produced using techniques known as "flame drawing".

In accordance with these techniques, primary solid filaments having a diameter of about one millimeter are introduced into a high-speed, high-temperature gaseous current. Under the action of this current, the filaments soften and are drawn into fine fibers which, under certain conditions, can be practically continuous. The felts made of these very fine fibers present the advantage of offering excellent insulating properties for very low masses, but the production technique is highly energy-intensive. For these reasons, their main uses are limited to specialized areas, for example, in the aeronautics industry, in which the questions of weight constitute a fundamental element of assessment and in which cost has a lower priority.

Be this as it may, in this utilization, the absorbent aspect of these felts does not appear. Quite on the contrary, attempts are made to preserve the hydrophobic properties as much as possible by adding special lubricants, for example, silicone products.

SUMMARY OF THE INVENTION

Development of this invention has shown that it is possible to utilize mineral wools to produce absorbent products and especially hygienic products, under comparable, if not more advantageous cost conditions than those corresponding to the use of the conventional materials, especially cellulose fluff.

It has also been shown that, in these uses, these absorbent materials present additional advantages, and especially better mechanical properties. Moreover, they are normally white in color.

The production of fine fibers in large quantities utilizing means which are typically employed for the production of insulating materials, is the basis of the invention, according to which, as an absorbent material, and specifically an absorbent material for principally aqueous physiological liquids, but possibly other liquids as well, such as solvents, inks . . . a felt made of mineral fibers, such as glass fibers, is utilized, the fineness of which is such that these fibers possess a specific surface area of at least 0.25 m²/g of fibers and preferably over 0.5 m²/g.

Typically, these specific surface areas correspond to fibers whose average diameter is always under 5 micrometers and even under 2.5 micrometers. But the materials according to the invention can still be appreciably finer. The average diameter of the fibers can even be under 1 micrometer.

As much as their fineness, it is important that these fibers be quite homogeneous, and especially that the material which is chosen be free of non-fibrated or clustered particles, the diameter of which could reach or exceed 20 micrometers.

Generally, the absorbent materials according to the invention are comprised of fibers whose diameters are between 0.5 and 2 times the average diameter.

DETAILED DESCRIPTION OF THE INVENTION

It is appropriate to emphasize here that the materials according to the invention have a fibrous structure. In fact, pulverulent materials are known, which have a very high specific surface area and, for this reason, are utilized as absorbents. Obviously, such materials cannot lead to uses which are comparable to those of the materials according to the invention. In addition to the typical cohesion of the fibrous materials, it is possible to distinguish fibrous materials from pulverulent materials by geometric characteristics. Fibrous materials have an extension, i.e., a very high length/diameter ratio, which, in all cases, is greater than 100, and is generally greater than 1000, while, in the case of the pulverulent materials, this ratio is close to unity and does not normally exceed 10.

In practice, as shown in reference to the examples, the length of the fibers utilized is advantageously several centimeters. Taking account of the aforementioned finenesses, the extension ratios are normally several thousands.

In addition to their fineness, the fibers must possess certain additional properties. Specifically, their arrangement in the felt, an arrangement which depends at once on the length and the manner in which the felt is formed as well as the subsequent treatments of the felt which is thus produced, this arrangement is advantageously isotropic. In other terms, the fibers inside the material must be oriented in an aleatory manner; in still other words, for the felt to offer the best absorbent characteristics, the fibers must not be arranged in any dominant direction.

In the case of absorbent products, the isotropic distribution is favorable, because it corresponds to small by-volume masses and thus to a high absorption capacity, with respect to the fiber mass. Moreover, this same arrangement promotes the felt's recovery of its thickness after it has been compressed. This property is advantageous to the extent where the production of these low mass by-volume products can involve a prolonged compression without substantial effects on the original properties of the product. The absorption capacity in fact depends on the porosity of the felt, i.e., in a descriptive manner, on the "available" space between the fibers. The lower the by-volume mass, the more absorbent the product is. The fact that the product recovers its thickness quite well after compression is thus a guarantee of its absorbent properties and this is the capacity in which this specific characteristic is important according to the invention.

The properties of "resistance" to compression mentioned above also intervene in other ways. For products with high absorption capacities, the problem of the sinking of the absorbent product under the effect of the mass of the absorbed liquid arises, which tends to reduce the absorption potential. If the product is clearly resistant to deformation, the absorption is greater for a same initial porosity. The phenomenon us increasingly perceptible as the thickness over which the product extends increases.

Moreover, the products undergo compression in their use properly speaking. It is important that the sinking of the material which has absorbed the liquid, and which is subject to this load or compression, be as low as possible. Quite obviously, the actual absorption capacity is dependent on this sinking.

With respect to the testing of the materials, the standardized measurement of absorption under pressure is conducted by applying a compression of 2,500 Pa. Under these conditions, the products according to the invention advantageously present a sinking in the moist state which is not greater than 30% and preferably not greater than 20%.

It is understood that these properties are promoted not only by the distribution, but also by the length of the fibers, with long fibers more easily imparting a "spring" effect to the felt.

Of course, the properties described above are embodied only when the fibers which are produced are free from structural defects which can cause them to break under the stress of compression. Specifically, the diameter of the fibers must not vary in significant proportions along a single fiber. Nonetheless, if their diameter must be relatively constant, these fibers can advantageously form loops or waves, which promote interlocking and isotropy. This latter characteristic constitutes a difference in the mineral fibers utilized according to the invention with respect to those which are produced according to flame drawing techniques mentioned above, with the latter having a form including few waves.

The isotropic properties of felts can be assessed experimentally by measuring, for example, their resistance to the passage of air in a perpendicular direction to their surfaces and in a direction which is parallel to these surfaces. The surfaces in question are determined upon the collection of the fibers produced. One of these surfaces is in contact with the collection conveyor, the other corresponds to the upper limit of the layer of fibers deposited on the conveyor. The closer these two resistances are to each other, the more isotropic the felt is. It is preferable to utilize felts whose air passage resistance, or isotropy ratio, is not greater than 2.

If the presence of isotropic fibrous structures is advantageous for absorption, in practice, it is nonetheless often noted that perfect isotropy is not reached. Traditional methods for the collection of newly-formed fibers, namely the "filtration" of the fibers on a conveyor belt which is gas permeable and which retains the fibers carried by the gas currents, promote an arrangement in the planes parallel to the collection conveyor.

This natural tendency is countered by the size of the fibers and especially by their waves and loops, as indicated above.

It still must be explained that an arrangement promoting the orientation in the planes which are parallel to the surfaces of the felt produced can present certain advantages, providing that it is not exclusive. Thus, it is noted that the tendency towards "stratification" following the planes parallel to the conveyor yields products in which the diffusion of the liquid absorbed is relatively quicker than in a perfectly isotropic material. According to the required properties, i.e., depending on the intended use, it can thus be advantageous to choose a partially stratified material, so as to increase the diffusion speed, even if this is achieved while slightly reducing the absorption capacity.

Due to the fineness and the mechanical characteristics of the fibers constituting the materials according to the invention, these fibers can reach relatively large specific volumes in the non-compressed state. Typically, a glass fiber-based absorbent material according to the invention has a volume of over 15 cm$^3$/gram of fiber and which is preferably greater than 20 cm$^3$/g, and can reach, and even exceed, 50 cm$^3$/g.

This characteristic also distinguishes the materials according to the invention from the pulverulent absorbent materials discussed above, which possess much lower specific volumes.

Taking account of this high specific volume, the absorption capacity of these materials is ordinarily greater that 15 g of water per gram of fiber, and, advantageously, greater than 20 g/g and can even exceed 25 g/g, when this capacity is measured in the absence of stress. When the measurement is reproduced with samples subjected to a standardized load of 2,500 Pa, the absorption capacity of the materials according to the invention is greater than 12 g of water per gram of fiber and for the preferred products, it is greater than 15 g/g.

EXAMPLES

In the tests summarized below, four materials according to the invention, designated respectively by references A, B, C and D, are compared to a fluff which is utilized industrially to make diapers.

The production method for glass wool is the type which is described in European Patent Publication No. 0 091 381.

In this production method, melted glass issuing from a melting furnace is poured into a centrifuging device.

Advantageously, the composition of the glass utilized corresponds to that which is defined in the aforementioned European patent, namely in the following gravimetric proportions:

| $SiO_2$ | 61–66 | $Na_2O$ | 12.55–16.5 |
|---|---|---|---|
| $Al_2O_3$ | 2.5–5 | $K_2O$ | 0–3 |
| CaO | 6–9 | $B_2O_3$ | 0–7.5 |
| MgO | 0–5 | $Fe_2O_3$ | under 0.6 |

The molten glass is brought to a temperature of about 1500° C., in the form of a continuous casting, in a distributing component placed inside the centrifuging component forming the fibers. The glass, divided into large threads (3 to 4 mm in diameter) is projected onto the internal peripheral wall of the centrifuge.

The centrifuge in endowed with a large number of openings, through which the glass escapes under the effects of centrifugal force. The openings are small, or about 1 mm in diameter.

The feed conditions, especially the temperature and flow rate of the glass, the centrifuge temperature, are controlled so as to maintain a continuous flow of material from the centrifuge openings.

The fine filaments projected through the openings in the centrifuge wall go through a hot, high-speed gaseous current, established so as to run along the centrifuge wall in a direction which is near its axis.

The filaments are pulled and drawn by these hot gasses which conventionally issue from an internal combustion burner.

The fibers which are formed harden upon contact with the surrounding air. They are collected on a gas permeable conveyor. On this conveyor, they are deposited in the form of a low byvolume mass felt, whose thickness is a function of the flow of the fiber formation device, the width of the conveyor and the speed at which it is moving. It is possible for the conditions to be adjusted so that the felt which is collected can be used directly to form the layer of absorbent material according to the invention, after it is cut in the appropriate sizes.

The absorbent fibrous materials according to the invention can be utilized as they are. The fibers can also be treated to improve their properties. One possible treatment consists, for example, of spraying the path of the fibers with a lubricating compound, before they are collected on the conveyor.

Contrary to insulation felts, the fibrous layers formed in accordance with the invention are not normally bound with resins. The natural cohesion of the layer of fibers is usually sufficient for the intended utilization. Moreover, the addition of a bonding resin, in addition to the supplementary cost it entails, generally causes a decrease in the hydrophilicity of the fibers. For all of these reasons, it is preferable not to bond the fibers, contrary to what is practiced in the area of insulation fibers.

However, if need be, a small proportion of a bonding agent which does not decrease the hydrophilicity, for example, a starch-based compound, can be utilized.

Other compounds can also be sprayed on the fibers, for example, to modify their texture.

The properties of the layers of absorbent materials according to the invention vary considerably, as we will see in the results given below, depending on the conditions under which they are produced. If, in a general manner, as we have already mentioned, the technique which is described in the cited European patent is utilized, specific conditions can be preferred to produce the best results.

Taking account of the intended applications, in the implementation of these techniques, the conditions which especially promote the fineness of the fibers and, to a lesser extent, their length, are, in fact, chosen, even if this choice leads to a relatively smaller yield.

In a practical manner, one of the advantages of the technique described in the aforementioned application is to regulate the action of the gaseous currents in the processes resulting in the drawing of the fibers. In fact, experience shows, for this type of technique, that, for a specific flow and a given degree of fineness for the fiber, the length of the fibers depends on the blowing conditions. The more intense the gaseous current, the finer, but also the shorter, the fibers are. Achieving the proper drawing without increasing the blowing, as provided according to the technique in question, thus allows fine fibers to be produced, in a relatively abundant quantities, and with satisfactory lengths for the considered use.

As emerges from the above information, materials which can be utilized according to the invention can be prepared under conditions which depart from the framework defined in the cited application, though to the detriment of the yield and entailing a production cost which remains as an important factor such that these materials are advantageously substituted for the conventional absorbent materials.

On an indicative basis, the materials were prepared by adjusting the mode of the hot gas generating burner so that the emission was effected at a speed of about 100 to 200 m/s and at a temperature of 1380° to 1550° C. The temperature of the centrifuge, under these conditions, was set between 920° and 1050° C.

Moreover, it is also obvious that, for a same device, i.e., notably for the same number of openings and the same ensuing number of filaments, the mass of the fibers produced varies as a function of their fineness. The finer the fibers are, the lower the mass.

The table below gives the mass of the fibers produced per day, for each centrifuge device, for the four materials according to the invention. The table also includes the specific surface area of each of the materials obtained and their mass volume.

| Fibers | Flow in $10^3$ kg/d | Specific Surface area in $m^2/g$ | Volume by mass, in $cm^3/g$ | Under a weight of 2,500 Pa |
|---|---|---|---|---|
| A | 0 | 0.20 | 24 | 19 |
| B | 10 | 0.75 | 32 | 20.3 |
| C | 7 | 1.25 | 35 | 22.7 |
| D | 4 | 2.6 | 38.5 | 25.6 |

The fibers produced are highly regular and free of heterogeneous particles such as those which can be found in insulating products and which are the result of defects in the fibers.

The fibers collected without treatment are white and soft to the touch. The impression is comparable to that of a cotton/wool wadding or cotton. The fibers, which are an average of about 3 to 4 cm long, are supple.

As a comparison, the cellulose fluff fibers are thicker, much shorter and their mass volume is slightly under about 20 $cm^3/g$.

Samples are prepared from these various materials, following well-defined dimensions, so as to test the absorbent properties.

In an initial series of tests, samples were prepared under the conditions proposed by Scandinavian standard SCAN C 33-80 for the measurements which are normally conducted for fluff.

The principle of the method is as follows:

Samples of absorbent, previously conditioned material (mass, shape, temperature, ...) are placed on a grid.

The grid, compressed under a uniformly distributed weight corresponding to 2,500 Pa is placed in contact with a layer of water. The sample becomes saturated. When equilibrium is reached, the grid is raised. The quantity of water absorbed is determined by the difference in the weight of the sample before and after contact with water.

During these tests, the time necessary for the water to progress from the contact surface to the upper surface of the material is simultaneously determined.

The results of these tests are summarized in the table below.

| Fibers | g/g Adsorption under 2,500 Pa | Wetting time(s) | Diffusion speed (mm/s) |
|---|---|---|---|
| Fluff | 9–11.6 | 4.8 | 4.6 |
| A | 12–15 | 8–12 | 2.3–3.4 |
| B | 14–19 | 8–12 | 2.4–3.6 |
| C | 19–21 | 12–14 | 2.3–2.7 |
| D | 13–16 | 20 | — |

Based on the above results, it is noted generally that the materials according to the invention are quite significantly better than fluff in the area of absorption capacity.

The absorption capacity for the best tests is practically doubled, and for the least successful, is increased by about 50%. The improvement is thus considerable.

The comparison of the four products according to the invention demonstrates the existing relations between the specific surface area and the absorption capacity. The greater the surface area, the greater the mass of water absorbed for the same mass of fibers.

This tendency is nonetheless limited by the relative sinking of the sample under the effect of the mass of liquid absorbed. A measurement of the heights of the sample, dry and saturated, clearly demonstrates this phenomenon. For this reason, sample D, comprised of the finest fibers, has a lower degree of absorption than sample C. The difference in absorption varies directly with the difference in height. If sample D, dry, is more voluminous than sample C, it undergoes sinking which, in the wet state, gives it a smaller volume than that of sample C. Even for this sample, it must be noted that the absorption capacity remains greater than that of the fluff.

If, in this table, the wetting time for the samples according to the invention appears to be greater, this does not imply that the absorption is slower. In fact, the wetting time corresponds to the time which is necessary for the liquid absorbed at the base of the sample to reach the highest point. Given that the samples according to the invention are higher than the fluff at the end of the test, or still, that they absorb more liquid, it is not surprising that this wetting time is greater. If this time is related to the height of the sample or the mass of liquid absorbed, it is then noted that the diffusion speed (or the absorption speed) has exactly the same magnitude as that of the fluff. The slight difference which can be noted results from the fact that the diffusion speed in the sample is related to the height of the sample. Diffusion is more rapid at the level of the liquid's contact with the surface, and decreases as the point in question is higher above this surface. Liquid diffusion measurements taken at identical heights on fluff samples on the one hand, and those of absorbent according to the invention on the other hand, show a great similarity for the fluff having the highest absorption speed. On the average, the same measurements conducted on fluffs of various origins, show an overall diffusion speed which is appreciably lower than with the absorbent products according to the invention.

Taking account of the results presented above, it emerges clearly that the materials according to the invention are highly appropriate for the production of absorbent products such as diapers and similar products discussed at the beginning of this text.

In this type of use, the absorbent materials in question can be utilized alone or combined with other absorbent products. It is especially possible to proceed with a mixture of glass fibers, such as those described above, with the conventionally used cellulose fluffs.

It is also possible, if need be, to mix glass fibers having different characteristics to give the mixture at once better absorption qualities related to the fineness, and a good degree of resistance to sinking in the wet state.

Product B according to the invention is mixed with a "fluff product", containing fluff fibers in various proportions. The variations of the properties of the product thus prepared are followed as a function of the gravimetric proportion of glass fibers.

| % Glass fibers | Mass volume cm³/g | Adsorption capacity under a weight a weight of 2,500 Pa |
|---|---|---|
| 0 | 24 | 8.0 |
| 10 | 26 | 9.2 |
| 20 | 28 | 10.0 |
| 30 | 29 | 10.2 |
| 50 | 30.5 | 12.2 |
| 100 | 33 | 15.8 |

The results of this table show a clear concurrence with those corresponding to the preceding tests. They show especially that the glass fibers according to the invention can be utilized with other absorbent materials to modify their characteristics, in particular the absorption capacity.

Besides the improvement of the absorption properties, the glass fiber is mixed with fluff to modify its mechanical properties. One of the characteristics of the fluff is, as we have mentioned, its lack of cohesion because it is comprised of extremely short fibers.

The improvement of the qualities of the fluff allows the utilization conditions to be modified. In practice, in fact, for the production of absorbent diapers, for example, the fluff must necessarily be placed inside covers which give the resulting structure the necessary dimensional characteristics and the choice of the material comprising this cover is determined by this imperative of resistance. The use of a material such as that of the invention allows, if not the elimination of the cover, at least fewer limitations in the choice of its characteristics.

Under the production conditions which were mentioned above, it is, moreover, important to emphasize that the cost of the absorbent material comprised of glass fibers, makes it a product which can be advantageously substituted for conventional materials, such as fluff. Even though the unit weight production cost is slightly higher, the performance achieved in the area of absorption allows a much smaller mass of fibers to be utilized for the same effect. Moreover, as we have seen, the choice of the materials according to the invention allows a considerable improvement of other properties, especially the mechanical properties.

On this subject, it must be emphasized that the absorption tests mentioned above were conducted on samples, whose properties were not altered by treatment and storage. In practice, of course, during these operations, the absorbent material is exposed to stresses, notably, it undergoes compression. The "elasticity" of the felts made of glass fibers allows these materials a good capacity to recover their initial properties when these stresses are removed. Thus, the absorbent properties are modified little or not at all. On the contrary, the fluff-based absorbent materials do not recover their initial properties.

It has been verified that the absorbent properties of the products according to the invention do not deteriorate when they are exposed to a prior, relatively great compression to simulate the modifications incurred for example during storage.

For this purpose, samples of product C are exposed to a compression in the sense of their thickness for one hour. The reduction in thickness corresponding to this compression is measured. The compression is released for 24 hours and absorption capacity measurements are next conducted under the conditions of the Scandinavian standard SCAN C 33-80 (i.e., under a compression of 2,500 Pa).

It is noted that, even for the most severe prior compression treatments, the absorption capacity of the products according to the invention is only relatively slightly altered.

| Prior compression | Thickness of sample (mm) | % Thickness reduction | Adsorption under 2,500 Pa (g/g) |
|---|---|---|---|
| 2,500 | 37 | 0 | 19 |
| 5,000 | 27 | 27 | 19 |
| 10,000 | 20 | 46 | 18.5 (−2.6%) |
| 20,000 | 14 | 62 | 17.7 (−8%) |

The advantage brought by the absorbent products according to the invention does not rest solely in their liquid retention capacity; their increased mechanical resistance is also observed, which makes their implementation more convenient.

This mechanical resistance was evaluated through the use of a penetration test conducted on samples prepared as for the SCAN C 33-80 test. The disc-shaped sample is supported on its periphery. A piston moving forward at a rate of 20 mm/min is applied to the center of the disc and determines the force which is necessary to puncture the sample. By reproducing the same conditions, a resistance 3 to 4 times greater than that of the conventional fluffs is observed for the products according to the invention.

What is claimed as new and desired to be secured by Letters Patent of the United States is:

1. In a hygenic product, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles.

2. In a hygenic product, the improvement comprising using an absorbent material in the form of interlaced mineral fibers having a specific area of at least 0.25 m²g⁻¹, wherein the diameter of the fibers does not vary significantly along a single fiber, and the fibers form loops or waves, said fibers having an average diameter under 5 μm, having a homogeneous size distribution and being free of non-fibrated or clustered particles.

3. The hygenic product of claim 1, wherein the said absorbent material in the form of a layer of interlaced mineral fibers possesses a specific surface area of at least 0.5 m²g⁻¹.

4. The hygenic product of claim 2, wherein the said absorbent material in the form of interlaced mineral fibers possess a specific area of at least 0.5 m²g⁻¹.

5. In a diaper, sanitary napkin, or bandage, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles.

6. In a diaper, sanitary napkin, or bandage, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles, said fibers being produced by passing molten glass through holes arranged in the periphery of a centrifuge, with the fibers produced, carried by gaseous current, being collected in the form of a felt on a collection component, with the collected felt undergoing carding operation to increase its mass volume.

7. In a diaper, sanitary napkin, or bandage, the improvement comprising using an absorbent material in the form of interlaced mineral fibers having a specific area of at least 0.25 m²g⁻¹, said fibers having an average diameter under 5 μm, having a homogeneous size distribution and being free of non-fibrated or clustered particles, wherein the diameter of the fibers does not vary significantly along a single fiber, and the fibers form loops or waves.

8. The diaper, sanitary napkin, or bandage of claim 5, wherein the said fibers have a specific surface area of between 0.5 and 1.5 m²g⁻¹.

9. The diaper, sanitary napkin, or bandage of claim 5, wherein the ratio of the average length of the fibers to their average diameter is greater than 100.

10. The diaper, sanitary napkin, or bandage of claim 5, wherein the specific volume of the said absorbent material in the non-compressed state is at least equal to 15 cm³ per gram of fibers.

11. The diaper, sanitary napkin, or bandage of claim 10, wherein the said specific volume is greater than 20 cm³ per gram of fibers.

12. The diaper, sanitary napkin or bandage of claim 5, wherein the said absorbent material has an absorption capacity by capillary action, under a pressure of 2500 Pa, greater than 12 g of water per gram of fibers.

13. The diaper, sanitary napkin, or bandage of claim 12, wherein the said absorbent capacity by capillary action, under a pressure of 2500 Pa, is greater than 15 g of water per gram of fibers.

14. The diaper, sanitary napkin or bandage of claim 13, wherein the sinking of the said absorbent material under a load of 2500 Pa is under 20%.

15. The diaper, sanitary napkin, or bandage of claim 5, wherein the said mineral fibers are mixed with another absorbent material, in a gravimetric proportion which is less than 10%/90%.

16. The diaper, sanitary napkin, or bandage of claim 15, wherein the said mineral fibers are mixed with cellulose fibers in a gravimetric proportion which is not under 50%/50%.

17. In a diaper, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles, fibers being produced by passing molten glass through holes arranged in the periphery of a centrifuge, with the fibers produced, carried by gaseous current, being collected in the form of a felt on a collection component, with the collected felt undergoing a carding operation to increase its mass volume.

18. In a diaper, the improvement comprising using an absorbent material in the form of interlaced mineral fibers having a specific area of at least 0.25 m²g⁻¹, said fibers having an average diameter of under 5 μm, having a homogeneous size distribution and being free of non-fibrated or clustered particles, wherein the diameter of the fibers does not vary significantly along a single fiber, and the fibers form loops or waves.

19. The diaper of claim 17 wherein the said absorbent material in the form of a layer of interlaced mineral fibers has a specific surface area which is at least 0.5 m²g⁻¹.

20. The diaper of claim 18, wherein the said absorbent material in the form of interlaced mineral fibers has a specific area of at least 0.5 m²g⁻¹.

21. In a sanitary napkin, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles, said fibers being produced by passing molten glass through holes arranged in the periphery of a centrifuge, with the fibers produced, carried by gaseous current, being collected in the form of a felt on a collection component, with the collected felt undergoing a carding operation to increase its mass volume.

22. In a sanitary napkin, the improvement comprising using an absorbent material in the form of interlaced mineral fibers having a specific area of at least 0.25 m²g⁻¹, said fibers having an average diameter diameter under 5 μm, having a homogeneous size distribution and being free of non-fibrous or clustered particles, wherein the diameter of the fibers does not vary significantly along a single fiber, and the fibers form loops or waves.

23. The sanitary napkin of claim 21, wherein the said absorbent material in the form of a layer of interlaced mineral fibers possesses a specific surface area of at least 0.5 m²g⁻¹.

24. The sanitary napkin of claim 22, wherein the said absorbent material in the form of interlaced mineral fibers possess a specific area of at least 0.5 m²g⁻¹.

25. In a bandage, the improvement comprising using an absorbent material in the form of a layer of interlaced mineral fibers whose specific surface area is at least 0.25 m²g⁻¹, said fibers having an average diameter under 5 μm, having a homogeneous size distribution and being free of non-fibrated or clustered particles, said fibers being produced by passing molten glass through holes arranged in the periphery of a centrifuge, with the fibers produced, carried by gaseous current, being collected in the form of a felt on a collection component, with the collected felt undergoing a carding operation to increase its mass volume.

26. In a bandage, the improvement comprising using an absorbent material in the form of interlaced mineral fibers having a specific area of at least 0.25 m²g⁻¹, said fibers having an average diameter under 5 μm, having a homogeneous size distribution and being free of non-fibrated or clustered particles, wherein the diameter of the fibers does not vary significantly along a single fiber, and the fibers form loops or waves.

27. The bandage of claim 25, wherein the said absorbent material in the form of a layer of interlaced mineral fibers possesses a specific surface area of at least 0.5 $m^2g^{-1}$.

28. The bandage of claim 26, wherein the said absorbent material in the form of interlaced mineral fibers possesses a specific area of at least 0.5 $m^2g^{-1}$.

* * * * *